United States Patent [19]

Metais

[11] Patent Number: 5,176,653
[45] Date of Patent: Jan. 5, 1993

[54] IMPROVEMENTS TO IMPLANTABLE VASCULAR ACCESS DEVICES

[76] Inventor: Joël Metais, La Cottenciée, 86420 Berthegon, France

[21] Appl. No.: 727,821

[22] Filed: Jul. 9, 1991

[51] Int. Cl.⁵ .................................. A61M 5/178
[52] U.S. Cl. ............................. 604/167; 604/175
[58] Field of Search ............ 604/167, 169, 170, 175, 604/88, 201, 205, 93, 244, 246, 51, 148

[56] References Cited

U.S. PATENT DOCUMENTS

| | | | |
|---|---|---|---|
| 4,569,675 | 2/1986 | Prosl et al. | 604/175 |
| 4,632,671 | 12/1986 | Dalton | 604/174 |
| 4,755,173 | 7/1988 | Konopka et al. | 604/167 |
| 4,955,861 | 9/1990 | Enegren et al. | 604/173 |
| 4,994,027 | 2/1991 | Farrell | 604/164 |
| 5,026,344 | 6/1991 | Dijkstra et al. | 604/93 |

FOREIGN PATENT DOCUMENTS

| | | |
|---|---|---|
| 0113520 | 11/1983 | European Pat. Off. |
| 0239244 | 2/1987 | European Pat. Off. |
| 0334116 | 3/1989 | European Pat. Off. |
| 3618390 | 5/1986 | Fed. Rep. of Germany |
| 2628639 | 3/1988 | France |
| 2185689 | 7/1987 | United Kingdom |

*Primary Examiner*—Cary E. O'Connor
*Attorney, Agent, or Firm*—Thomas R. Morrison

[57] ABSTRACT

Telescopic needles permit the perforation of implantable vascular accesses sealed by means of a flexible elastomeric membrane using needles of large diameter. The telescopic needles in order of increasing diameter, permit progressive perforation with widening of the orifice formed in the septum, with only the nozzle of greatest diameter remaining through the septum at the end of the operation.

The invention extends the area of application of implantable vascular access devices.

7 Claims, 3 Drawing Sheets

IMPROVEMENTS TO IMPLANTABLE VASCULAR ACCESS DEVICES

BACKGROUND OF THE INVENTION

The invention relates to improvements to implantable vascular access devices.

Implantable vascular accesses are used mainly in cases where repeated operations involving puncturing (sampling), dialysis (treatment), chemotherapy treatment, perfusion feeding, or other operations of this type, have to be repeated periodically a great many times over a long period.

The known devices essentially comprise a chamber in the form of a flat capsule lodged under the skin, communicating with a vein, the chamber being sealed on the skin side by a membrane called a "septum" made of elastomer or silicon and which is possible to perforate a great number of times without impairing the leakproofness of the system. So as not to damage the septum, it is essential that the puncturing be carried out with the aid of special needles with a bevelled head, of small diameter, not exceeding an external diameter of 0.7 mm.

This limitation on the diameter of the needles which can be used constitutes a major disadvantage, which means that such vascular accesses cannot be used for the perfusion of high-viscosity solutions, particularly for feeding or various chemotherapy treatments, nor for the rapid perfusion of large volumes, as in the case of blood transfusions, nor for taking from the body samples of blood for analysis or purification, in particular in a dialysis treatment.

Under these conditions, for all of the interventions of the type mentioned above, and many others, it is necessary to have recourse to external catheters which have serious disadvantages, especially with respect to the risk of infection which their use involves, or which are at the origin of accidents due to voluntary or accidental tearing-out of the catheter, these devices moreover being very uncomfortable for the patient.

The invention relates to improvements to implantable vascular access devices, permitting the use of such accesses even in cases where high flow rates are used, both for sampling and for feeding, or in cases where solutions of high viscosity are used, making it necessary to employ access channels of considerable diameter.

OBJECTS AND SUMMARY OF THE INVENTION

In order to achieve these aims, the implantable vascular access device according to the invention, of the type comprising a septum implanted under the skin and capable of being perforated several times by means of intervention needles, is characterised in such a way as to allow the passage of needles of greater diameter, without damaging the septum, there is provided, for passing through the septum, a system comprising at least one fine sharp-pointed introducing and guiding needle or mandrel on which there slides in a telescopic manner an intervention needle in the form of a nozzle of appropriate diameter suitably connected to the external apparatus for sampling, treatment or feeding, making it possible for the introducing mandrel, after positioning of the intervention nozzle through the septum, to be withdrawn rearwards in order to free the internal volume of the nozzle.

According to a preferred embodiment, the nozzle comprises to its rear a chamber sealed on one face by a perforatable membrane through which the mandrel can pass and which is directed essentially perpendicular to the axis of the nozzle, the chamber being connected to the external apparatus for treatment, sampling or feeding.

According to another characteristic of the invention, in order to improve the leakproofness characteristics of the septum and to prolong its service life, it advantageously consists of several superimposed layers of silicone leaves compressed together.

According to a still further improved embodiment, two septums are provided on the implantable device, the main one sealing the chamber in communication with the vascular access when a control membrane is in a first position for treatment, sampling or feeding, the other secondary control septum sealing a secondary chamber connected likewise to the vascular access when the control membrane is in a second position before or after treatment, the vascular access thus being in communication either with the main chamber or with the secondary chamber depending on the position occupied by the said control membrane.

The invention and its use will appear more clearly from the description which follows and in which reference is made to the attached drawings, in which:

DETAILED DESCRIPTION OF THE PREFERRED EMBODIMENT

Figure 1:
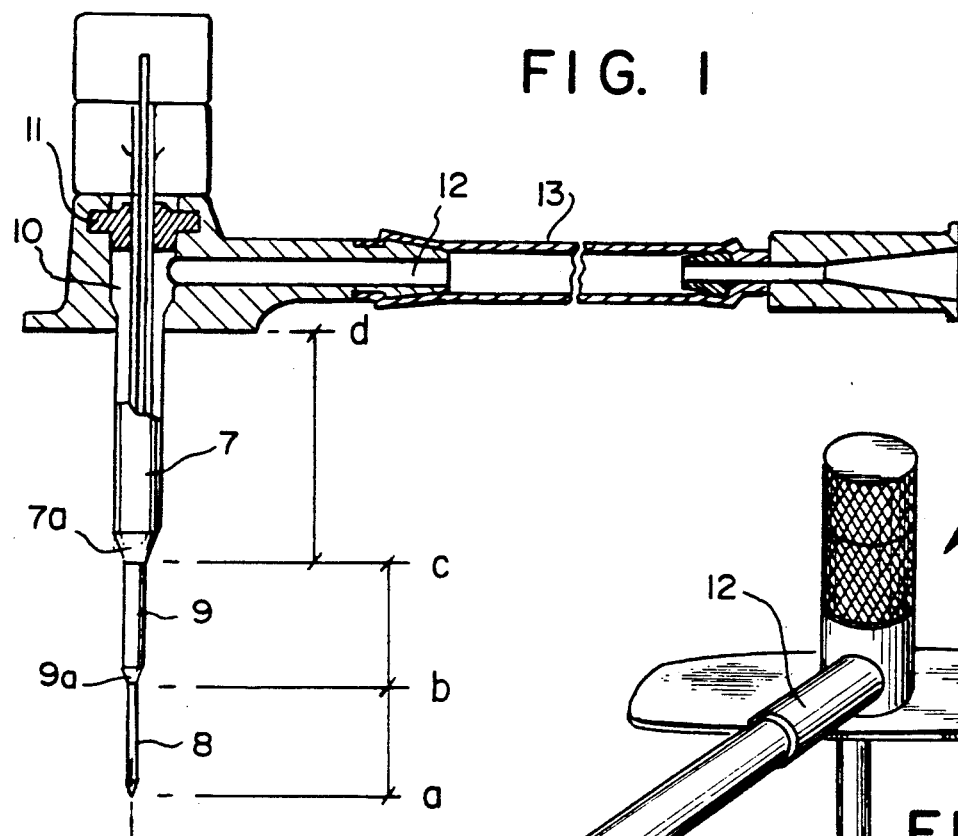
FIG. 1 shows diagrammatically in cross-section the improved system permitting the perforation of a septum, without damage, by means of a nozzle of a diameter very much greater than the maximum diameter which can currently be used in relation to this type of device, which nozzle can be in communication with the external apparatus for treatment (dialysis, feeding, etc.)
Figure 2:
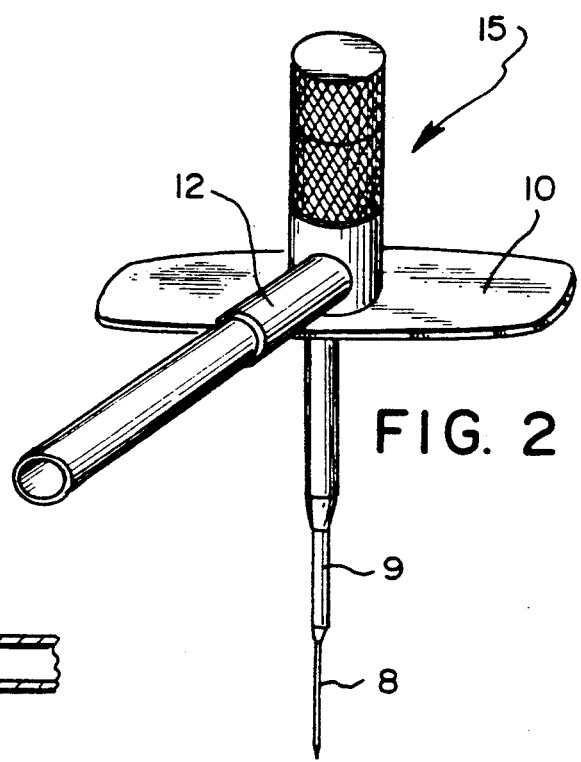
FIG. 2 shows a perspective view of the device in FIG. 1.
Figure 3:
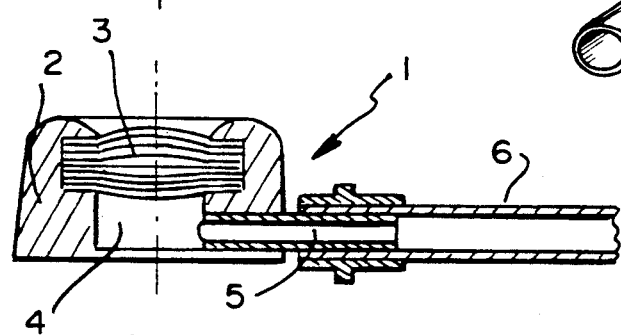
FIG. 3 shows a cross-section of the part of the implantable device comprising an improved septum which can be used together with the intervention device illustrated in FIGS. 1 and 2.

Reference will be made first to FIGS. 1, 2 and 3, with regard to which the implementation of the invention will be explained.

FIG. 3 illustrates an implantable vascular access device designated as a whole by 1 and essentially comprising a body 2 which is made of titanium or synthetic resin and which is sealed in its upper part by a flexible elastic partition 3 called a "septum", thereby delimiting a chamber 4 which is in communication via a conduit 5 with a catheter 6 appropriately connected to a vascular access. In the implanted position, the whole device is lodged under the skin of the patient, thereby avoiding the risks of infection associated with external accesses.

As stressed hereinabove, the disadvantage of the system is the limitation of its use, it being possible for the septum 3 to be perforated a great many times only with needles which are excessively fine, prohibiting the use of these systems in many applications. In practice, the needles of maximum diameter which can be used have an external diameter limited to 0.7 mm.

According to the invention, it will be possible to pass through the septum a nozzle, such as designated by 7, having a much greater external diameter, for example up to 2 mm, or an internal diameter of 1.6 mm, on account of the fact that the septum 3 is perforated and pierced through in a gradual manner, successively by means of a mandrel 8 formed by a needle with a sharp conical point, on which there is guided and slides a hollow needle 9 of greater diameter with a truncated end 9a which itself serves to guide the nozzle 7, which is of greater diameter and has a truncated end 7a.

The dimensions of a device, such as illustrated in FIG. 1, having proven entirely satisfactory are given hereinbelow.

The mandrel 8 has an external diameter of 1.2 mm at its widest part and terminates in a fine conical point. The intermediate needle 9 has an external diameter of 1.6 mm, the truncated part 9a inclined at approximately 30° to the axis permitting the progressive transition of the diameter from 1.2 to 1.6 mm. The nozzle 7 having an external diameter of 2 mm terminates in a nozzle 7a having an angle at the tip of approximately 30°, permitting progressive transition of the external diameter from 1.6 mm to 2 mm. When the device is in the position (before intervention) where the mandrel 8 and the intermediate needle 9 project over their entire length through the device, the mandrel 8 extends by a length ab=25 mm beyond the end of the needle 9, which itself extends by the length bc=25 mm beyond the end of the nozzle 7, which projects by the length cd of the order of 30 mm below the supporting and handgrip plate 10 of the intervention device.

With regards to the nozzle 7, it will be seen that this communicates via its proximal or rear end with a chamber 10 sealed at the rear by a septum 11, such as a silicone membrane, the chamber 10 being in communication via a pipe 12 with a tube 13 for connection to the external treatment apparatus (not shown).

The functioning of the device can be easily explained, especially with reference to the diagrams in FIGS. 5 to 8.

Figure 5:
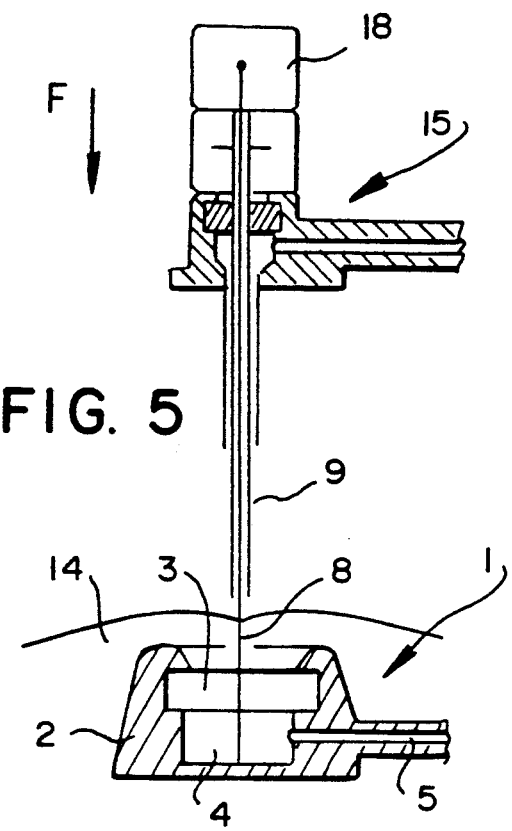
FIGS. 5, 6, 7 and 8 are diagrammatic sectional views showing four successive stages of an intervention for introducing through the septum the access nozzle according to the invention, permitting communication between the treatment apparatus and the vascular system of the patient.

In a first stage, the mandrel forming a sharp needle 8 is introduced through the septum 3, as illustrated in FIG. 5, by pushing the whole intervention device 15 in the axis of the needle 8. Since it is a mandrel with a fine sharp point, it forms only a pin-sized hole through the septum 3, without tearing or removal of material. And on account of the progressive nature of the increase in the external diameter of the mandrel 8, this hole widens and deforms elastically up to the external diameter of 1.2 mm of the mandrel.

Figure 6:
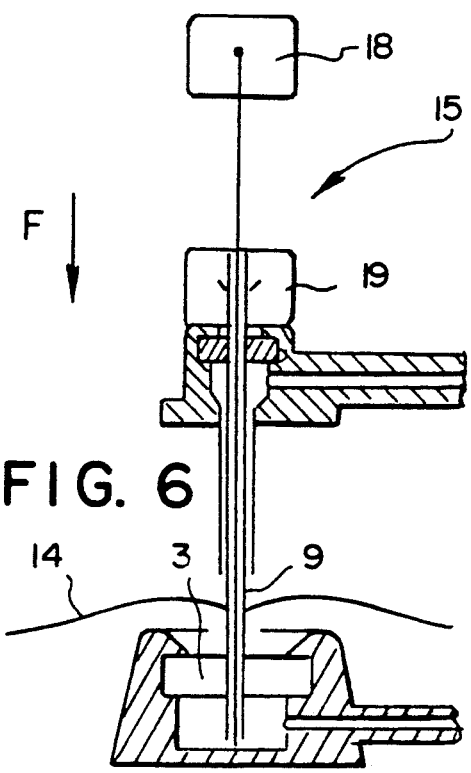
Figure 7:
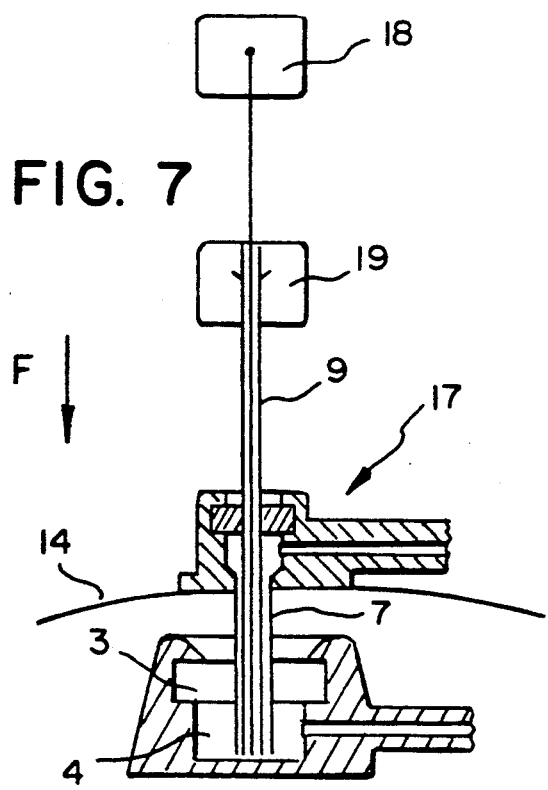

In a second stage, as illustrated in FIG. 6, the handle 19 integral with the intermediate needle 9 is lowered relative to the handle 18 integral with the mandrel 8, sliding this needle over the mandrel 8 by lowering it in the direction of the arrow F. During this, the orifice formed in the septum 3 continues to deform elastically and will now adapt to the external diameter of 1.6 mm of the needle 9.

In a third stage, the assembly 17 connected to the nozzle 7 is lowered by sliding it on the needle 9, still in the direction of the arrow F, the orifice formed in the septum 3 still widening elastically up to 2 mm.

Figure 8:
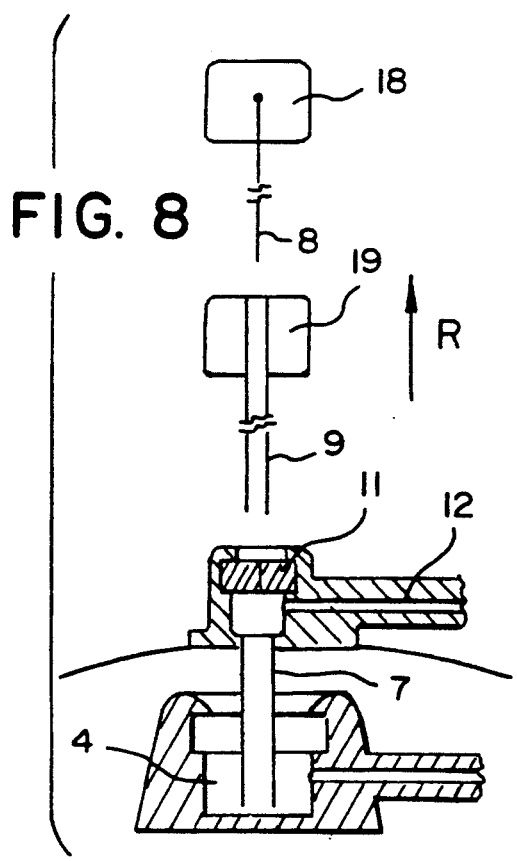

At this point, as illustrated in FIG. 8 by the arrow R, it is possible to withdraw the needle 9 and the mandrel 8 which had been introduced previously through the septum 11 of the assembly 17, which effects the leakproof communication of the external access 12 with the chamber 4 of the implanted device, and this via the nozzle 7 of appropriate diameter.

Figure 4:
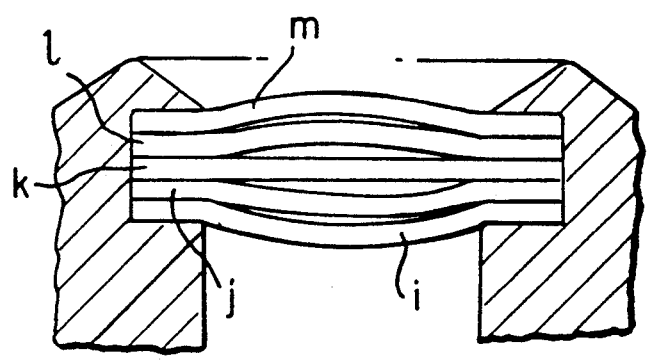
FIG. 4 shows on a larger scale the details of a septum consisting of several superimposed layers, as shown diagrammatically in FIG. 3.

In order to improve the leakproof character of the septum 3, it can advantageously be formed, as illustrated in FIG. 3 and more precisely in FIG. 4, by several superimposed layers of silicone, for example twelve layers of 0.5 mm (of which only five have been shown and designated i to m in the drawings for greater clarity). There may be advantageously provided between each layer of silicone an intermediate layer of a film of a product for self-closure of the perforations, such as a silicone which polymerises upon contact with humidity. Thus, after withdrawal of the nozzle 7 upon completion of an intervention, any possible microperforation will tend to close automatically.

Similarly, at least the outer layers, such as i and m, will advantageously be strengthened by means of synthetic fibres in such a way as to limit the deformations, the whole assembly being mounted compressed in the body 2, in a conventional manner.

Figure 9:
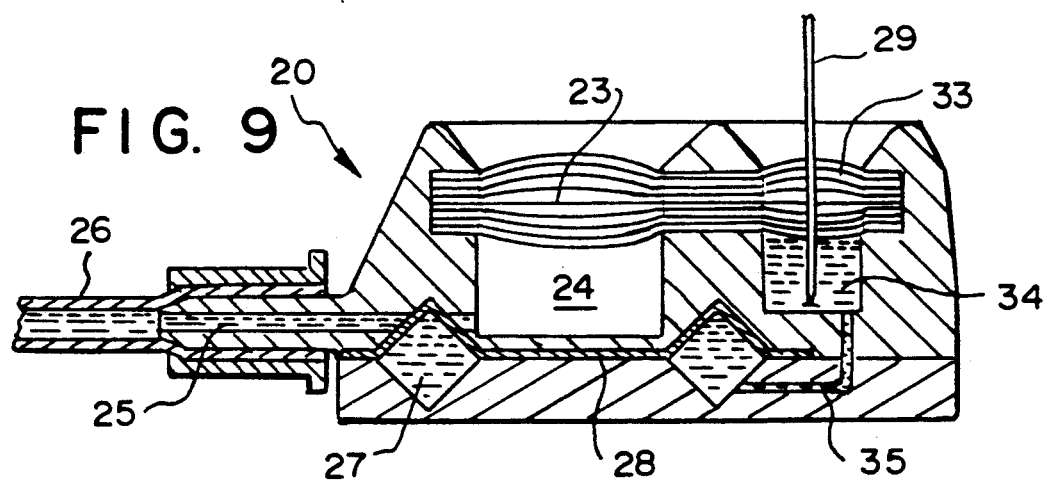
FIG. 9 shows in cross-section an improved implantable septum device with two chambers, the device being shown in one of its two functioning positions.
Figure 10:
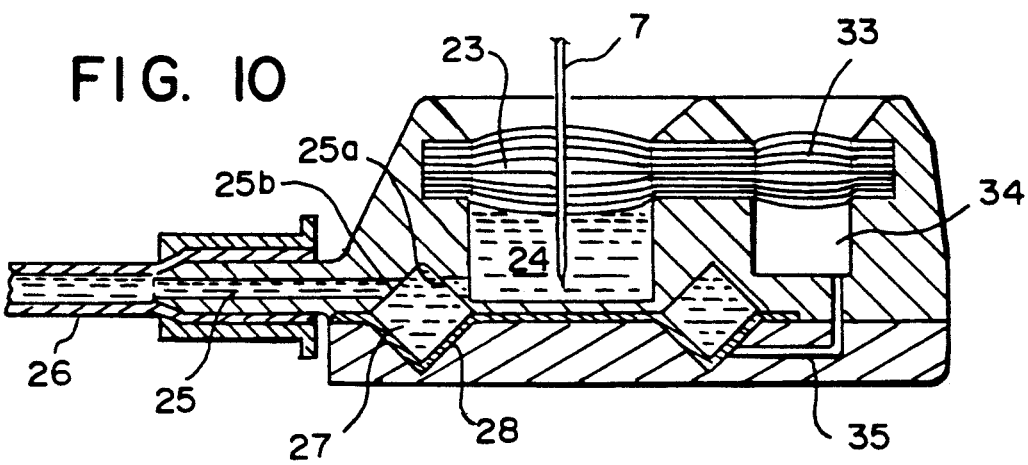
FIG. 10 shows the same device as in FIG. 9, but with the device in its second functioning position.
Figure 11:
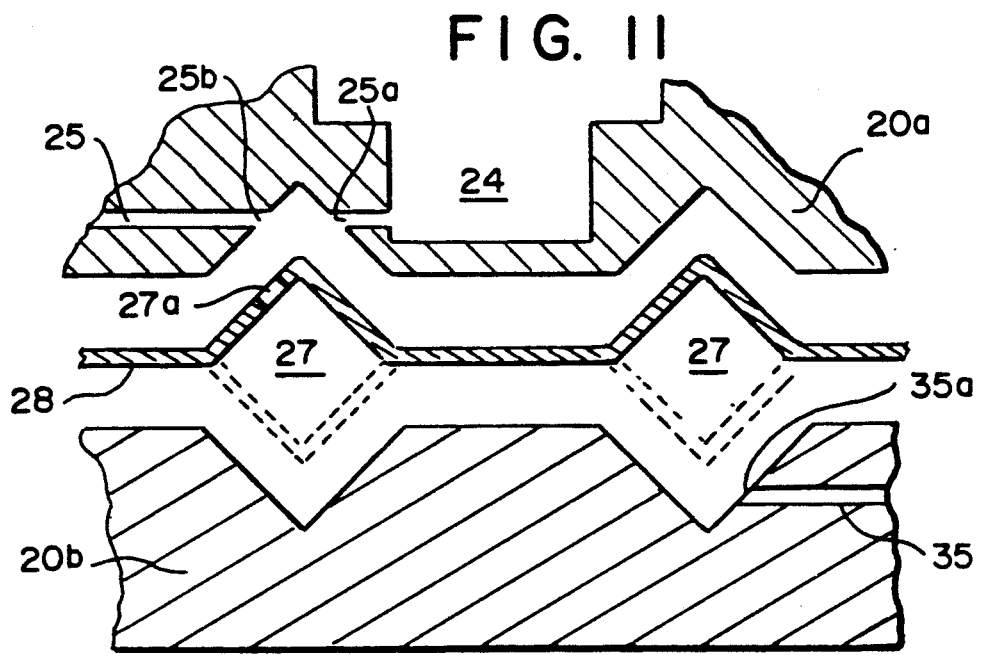
FIG. 11 shows on a larger scale, in an exploded view and with partial cutting away, the superposition of three essential parts of the device illustrated in FIG. 9.

According to the improvement shown in FIGS. 9 to 11, the implantable device, designated as a whole by 20, comprises a main chamber consisting, in a manner completely similar to the device 1 described previously, of a septum 23 sealing a chamber 24 in communication with the vascular access 26 via a tube 25.

However, alongside this main septum 23, there is a secondary septum 33 sealing a chamber 34 which can be brought into communication via a channel 35 with the vascular access 26 through an annular chamber 27 and the conduit 25, and this depending on the position occupied by a membrane 28, as will be described.

As emerges from FIG. 11, the membrane 28, which is advantageously a flexible membrane made of silicone, is mounted compressed between the upper part 20a of the device and the lower part 20b which closes it like the bottom of a watch case. Arranged between the bottom 20b and the part 20a is an annular chamber 27 in which the membrane 28 has play, being able to take up two positions, either the one in which it is turned upwards, as illustrated in FIG. 9, or the one in which it is turned downwards, as illustrated in FIG. 10.

The functioning of the device is as follows.

If a fine intervention needle the of conventional type, designated 29, is introduced through the septum 33 and a pressurized fluid such as, for example, physiological serum is introduced through this needle, the chamber 34 is filled and the annular chamber 27 is pressurized via the channel 35 by keeping the membrane 28 in the position illustrated in FIG. 9 or moving it into this position. In this position it will be seen that the membrane 28 occludes the access channel 25 between the chamber 24 and the vascular access 26, more precisely at the outlet 25a from the chamber 24 towards the annular chamber 27. And in this position, the annular chamber 27, which is in communication with the channel 35, is likewise in communication with the vascular access 26 by way of the orifice 27a formed in the membrane 28 in line with the outlet 25b of the channel 25 into this annular chamber 27.

If, in contrast, as illustrated in FIG. 10, intervention is carried out in the main chamber 24 by means of the intervention nozzle 7, the annular chamber 27 is pressurized, but this time from above and not from below, and the membrane 28 is kept in the position illustrated in FIG. 10 or is moved into this position, ensuring the communication between the chamber 24 and the vascular access 26 and sealing the communication with the chamber 34 because of the membrane 28 which comes to bear against the outlet 35a of the channel 35 into the chamber 27.

The advantage of the device is that it permits, especially at the start of treatment, the introduction of small quantities of a fluid, such as physiological serum, at a high pressure with a view to permitting the unblocking of the access if the latter, not having been used for several days for example, were to be blocked by blood clots, and this without the risk of discharge at the level of the inactive main septum 23.

This device also makes it possible, after all interventions, to replace the membrane 28 in the position illustrated in FIG. 9, thereby ensuring a double sealing of the device with the vascular access 26 at the level of the main chamber 24.

Given the large diameters of the nozzles such as 7 which can be used, and their plane face, it will be advantageous for the bottom of the chamber 24 to be ribbed or grooved in such a way as to prevent sealing of the device, particularly during a suction operation, if the nozzle 7 comes to bear against the bottom of the chamber 4 or 24.

The invention is not limited to the embodiments illustrated and described.

Thus, in particular, although the system for progressive introduction described uses, for withdrawing the mandrel 8 and the intermediate needle 9 for positioning of the nozzle 7, a system with a septum 11 for introduction/removal, it would be possible to conceive of other systems, for example the simple lifting, through a leak-proof ring 11, of the intermediate needles 8, 9 into an upper position in the chamber 10.

With regards to the material constituting the mandrel 8 and the needles 9 and 7, use may be made for example of stainless steels or else, in particular for the needles 9 and 7, of a compatible plastic material such as FEP (fluorinated ethylene-propylene) or PTFE (polytetrafluoroethylene).

I claim:

1. An implantable vascular access device comprising:
   at least one chamber in communication with a vascular access;
   at least one septum closing an upper face of said chamber;
   said septum including means for permitting spatially and temporally a plurality of perforations by a needle;
   said septum comprising a plurality of superimposed layers of silicone leaves compressed together, said layers including between each pair thereof a film of a product for self-closing said perforations;
   said needle including at least one fine, sharp-pointed introducing and guiding mandrel;
   a nozzle of appropriate diameter slidably mounted in a telescopic manner on said mandrel;
   said nozzle having a chamber in a rearward portion thereof;
   said chamber being sealed on a face thereof by a perforatable membrane through which said mandrel can pass;
   said perforatable membrane being directed essentially perpendicular to an axis of said nozzle;
   said chamber being connected to an external apparatus; and
   said mandrel disposed to be withdrawn rearward after a positioning of said nozzle through said septum.

2. A device as in claim 1, in which at least some of said layers are strengthened by a tissue of synthetic fibers.

3. A device as in claim 1 comprising:
   a first and a second septum;
   a first and a second chamber associated with said first and said second septum and proximal to lower surfaces thereof;
   a control membrane;
   said first septum sealing said first chamber when said control membrane is in a first position; and
   said second septum sealing said second chamber when said control membrane is in a second position.

4. A device as in claim 3 in which:
   said first and said second septum are disposed side by side;
   an annular chamber below said first and said second chambers;
   said control membrane is being a circular disk having an annular bulge toward its circumference;
   said first chamber emptying on one side of said control membrane into said annular chamber; and
   said second chamber being sealed off by said control membrane.

5. A device as in claim 4 wherein said communication with said vascular access being sealed off by said control membrane, according to its position, either with one chamber or with the other.

6. A device as in claim 1 comprising:
   a first and a second chamber in communication with a vascular access;
   a first and a second septum closing respectively upper faces of said first and second chambers;
   a control membrane;
   said first chamber being closed with said access and said second chamber being opened with said access when said control membrane is in a first position, and
   said second chamber being opened with said access and said first chamber being closed with said access when said control membrane is in the second position.

7. An implantable vascular access device comprising:
   a septum implanted under the skin;
   said septum including means for permitting spatially and temporally a plurality of perforations by a needle;
   said septum comprising a plurality of superimposed layers of silicone leaves compressed together, said layers including between each pair thereof a film of a product for self-closing said perforations;
   said septum having a chamber;
   said chamber having a bottom surface; and
   said bottom surface including ribs.

* * * * *